US012622924B2

(12) United States Patent
Barritault et al.

(10) Patent No.: US 12,622,924 B2

(45) Date of Patent: May 12, 2026

(54) COMPOSITION FOR THE PROTECTION AND REPAIR OF THE BLOOD BRAIN BARRIER

(71) Applicants: Centre National de la Recherche Scientifique, Paris (FR); Organes Tissus Regeneration, Reparation, Remplacement, Paris (FR); Denis Barritault, Paris (FR); Université de Caen Normandie, Caen (FR)

(72) Inventors: Denis Barritault, Paris (FR); Myriam Bernaudin, Bernières-sur-Mer (FR); Omar Touzani, Villy-Bocage (FR); Jérôme Toutain, Ondefontaine (FR); Yacine Khelif, Paris (FR)

(73) Assignees: Denis Barritault, Paris (FR); Centre National De La Recherche Scientifique, Paris (FR); Organes Tissus Regeneration, Reparation, Remplacement, Paris (FR); Université de Caen Normandie, Caen (FR)

( * ) Notice: Subject to any disclaimer, the term of this patent is extended or adjusted under 35 U.S.C. 154(b) by 805 days.

(21) Appl. No.: 17/595,818

(22) PCT Filed: Apr. 30, 2020

(86) PCT No.: PCT/EP2020/062081

§ 371 (c)(1),
(2) Date: Nov. 24, 2021

(87) PCT Pub. No.: WO2020/239356

PCT Pub. Date: Dec. 3, 2020

(65) Prior Publication Data

US 2022/0152089 A1 May 19, 2022

(30) Foreign Application Priority Data

May 27, 2019 (FR) ...................................... 1905566

(51) Int. Cl.

*A61K 31/737* (2006.01)
*A61K 31/728* (2006.01)
*A61P 25/28* (2006.01)

(52) U.S. Cl.

CPC .......... *A61K 31/737* (2013.01); *A61K 31/728* (2013.01); *A61P 25/28* (2018.01)

(58) Field of Classification Search

CPC .............................. A61K 31/737; A61P 25/28
See application file for complete search history.

(56) References Cited

U.S. PATENT DOCUMENTS

| | | | |
|---|---|---|---|
| 4,439,450 | A | 3/1984 | Coleman |
| 6,689,741 | B2 | 2/2004 | Barritault et al. |
| 7,396,923 | B2 | 7/2008 | Petit et al. |
| 2001/0023246 | A1 | 9/2001 | Barritault et al. |
| 2009/0062208 | A1 | 3/2009 | Mochly-Rosen et al. |
| 2012/0165259 | A1 | 6/2012 | Ueda |
| 2013/0287725 | A1 | 10/2013 | Barritault et al. |
| 2014/0256820 | A1 | 9/2014 | Takata et al. |
| 2014/0301972 | A1 | 10/2014 | Barritault et al. |
| 2017/0100428 | A1 | 4/2017 | Schlessinger et al. |
| 2018/0125880 | A1 | 5/2018 | Barritault |
| 2018/0161372 | A1 | 6/2018 | Bernaudin et al. |

FOREIGN PATENT DOCUMENTS

| | | | |
|---|---|---|---|
| CN | 101632728 | B | 8/2013 |
| CN | 107809999 | A | 3/2018 |
| CN | 107864626 | A | 3/2018 |
| EP | 0464759 | A2 | 1/1992 |
| EP | 3097928 | A1 | 11/2016 |
| JP | 2002-521503 | A | 7/2002 |
| WO | 9526739 | A2 | 10/1995 |
| WO | 00/05270 | A1 | 2/2000 |
| WO | 0151003 | A2 | 7/2001 |
| WO | 03046014 | A1 | 6/2003 |
| WO | 2005041986 | A2 | 5/2005 |
| WO | 2011/019023 | A1 | 2/2011 |
| WO | 2011156445 | A1 | 12/2011 |
| WO | 2012/081713 | A1 | 6/2012 |
| WO | 2018207792 | A1 | 11/2018 |

OTHER PUBLICATIONS

Mao, Molecules 2016, 21, 75. (Year: 2016).*
Pires, J. Med. Chem. 2015, 58, 4066-4072. (Year: 2015).*
Pereira, Glycoconjugate Journal (2022) 39:107-130. (Year: 2022).*
Adjou, Journal of General Virology (2003), 84, 2595-2603. (Year: 2003).*
Abdullahi, Am J Physiol Cell Physiol 315: C343-C356, 2018. (Year: 2018).*
Mangoni, Int. J. Radiation Oncology Biol. Phys., vol. 74, No. 4, pp. 1242-1250, 2009. (Year: 2009).*
Kapoor, Indian Journal of Dermatology 2011; 56(3). (Year: 2011).*
Abdullahi et al. "Blood-Brain Barrier Dysfunction in Ischemic Stroke: Targeting Tight Junctions and Transporters for Vascular Protection." Am J Physiol Cell Physiol. 2018;315:C343-C356.
Barritault et al. "RGTA® or ReGeneraTing Agents mimic heparan sulfate in regenerative medicine: from concept to curing patients." Glycoconj J. 2017;34:325-338.
Blaney et al. "Intrathecal mafosfamide: a preclinical pharmacology and phase I trial." Journal of Clinical Oncology. 2005;23(7):1555-1563.
Cardoso et al. "Looking at the blood-brain barrier: molecular anatomy and possible investigation approaches." Brain Research Reviews. 2010;64:328-363.

(Continued)

*Primary Examiner* — Layla D Berry
(74) *Attorney, Agent, or Firm* — ArentFox Schiff LLP

(57) ABSTRACT

The present invention relates to a pharmaceutical composition for its application as a drug, in particular for use in the protection of the blood-brain barrier and/or the repair and/or the restoration of the blood brain barrier. The present invention finds an application in particular in the therapeutic, pharmaceutical and veterinary fields.

11 Claims, 2 Drawing Sheets

(56) References Cited

OTHER PUBLICATIONS

Erickson et al. "Neuroimmune Axes of the Blood-Brain Barriers and Blood-Brain Interfaces: Bases for Physiological Regulation, Disease States, and Pharmacological Interventions." Pharmacol. Rev. 2018;70:278-314.
Garrigue et al. "Single photon emission computed tomography imaging of cerebral blood flow, blood-brain barrier disruption, and apoptosis time course after focal cerebral ischemia in rats." Int J Stroke. 2016;11(1):117-126.
Hone et al. "Biphasic Blood-Brain Barrier Openings after Stroke." Neurol Disord Stroke Int. 2018;1(2):1011.
Hynes et al. "Overview of the matrisome-an inventory of extracellular matrix constituents and functions." Cold Spring Harb Perspect Biol. 2012;4:a004903.
Khelif et al. "A heparan sulfate-based matrix therapy reduces brain damage and enhances functional recovery following stroke." Theranostics. 2018;8(21):5814-5827.
Marks Jr, et al. "Safety and tolerability of intraputaminal delivery of CERE-120 (adeno-associated virus serotype 2-neurturin) to patients with idiopathic Parkinson's disease: an open-label, phase I trial." The Lancet Neurology. 2008;7:400-408.
Möbius-Winkler et al. "How to improve endothelial repair mechanisms: the lifestyle approach." Expert Review of Cardiovascular Therapy. 2010;8(4):573-580.
Peschillo et al. "A comparison of acute vascular damage caused by ADAPT versus a stent retriever device after thrombectomy in acute ischemic stroke: a histological and ultrastructural study in an animal model." J Neurointerv Surg. 2016;0:1-7.
Rafii et al. "A phase1 study of stereotactic gene delivery of AAV2-NGF for Alzheimer's disease." Alzheimer's & Dementia, 2013;1-11.
Rajendran et al. "The vascular endothelium and human diseases." Int J Biol Sci. 2013;9(10):1057-1069.
Ronaldson et al. "Targeting transporters: promoting blood-brain barrier repair in response to oxidative stress Injury." Brain Research. 2015;1623:39-52.
Sharif et al. "The Blood Brain Barrier: A Review of its Anatomy and Physiology in Health and Disease." Clin Anat. 2018;1-34.
Sifat et al. "Blood-brain barrier protection as a therapeutic strategy for acute ischemic stroke." The AAPS Journal. 2017;19(4):957-972.
Steiner et al. "The heparan sulfate proteoglycan agrin contributes to barrier properties of mouse brain endothelial cells by stabilizing adherens junctions." Cell Tissue Res. 2014;358:465-479.
Sweeney et al. "Blood-brain barrier breakdown in Alzheimer disease and other neurodegenerative disorders." Nat Rev Neurol. Mar. 2018;14(3):133-150.
Teng et al. "Endothelial trauma from mechanical thrombectomy in acute stroke: in vitro live-cell platform with animal validation." Stroke. 2015;46:1099-106.
Thomsen et al. "The vascular basement membrane in the healthy and pathological brain." J Cereb Blood Flow Metab. 2017;37(10):3300-3317.
Warren. "Beyond the Blood: Brain Barrier: The Importance of Central Nervous System (CNS) Pharmacokinetics for the Treatment of CNS Tumors, Including Diffuse Intrinsic Pontine Glioma." Front. Oncol. 2018;8:Article 239.
Wilgus. "Growth Factor-Extracellular Matrix Interactions Regulate Wound Repair." Advances in Wound Care. 2012;1(6):249-254.
Kornev et al. "Hydrogel-assisted neuroregeneration approaches towards brain injury therapy: A state-of-the-art review." Computational and Structural Biotechnology Journal. 2018;16:488-502.
Gopalakrishnan et al. "Hydrogel Scaffolds: Towards Restitution of Ischemic Stroke-Injured Brain." Transl. Stroke Res. 2018;10(1):1-18.
Tammi et al. "Hyaluronan metabolism in skin." Progress in Histochemistry & Cytochemistry. 1994;29(2):1-82.
Stern et al. "Hyaluronan fragments: An information-rich system." European Journal of Cell Biology. 2006;85:699-715.
Ikeda et al. "Synthesis and biological activities of a library of glycosaminoglycans mimetic oligosaccharides." Biomaterials. 2011;32:769-776.
Barritault et al. "RGTA®-based matrix therapy—A new branch of regenerative medicine in locomotion." Joint Bone Spine. 2016;1-10.
Frescaline et al. "Glycosaminoglycan Mimetic Associated to Human Mesenchymal Stem Cell-Based Scaffolds Inhibit Ectopic Bone Formation, but Induce Angiogenesis In Vivo." Tissue Eng Part A. 2013; 19(13-14):1641-1653.
Jacquet-Guibon et al. "Randomized controlled trial demonstrates the benefit of RGTA® based matrix therapy to treat tendinopathies in racing horses." PLoS One. 2018;13(3):e0191796.
Holmes et al. "Heparan sulfate proteoglycans mediate internalization and propagation of specific proteopathic seeds." Proc Natl Acad Sci USA. 2013;110(33):E3138-3147.
Ouidja et al. "Structure-activity studies of heparan mimetic polyanions for anti-prion therapies." Biocshem Biophys Res Commun. 2007;363(1):95-100.
International Search Report and Written Opinion mailed Jul. 14, 2020 issued in PCT Application No. PCT/EP2020/062081.

* cited by examiner

COMPOSITION FOR THE PROTECTION AND REPAIR OF THE BLOOD BRAIN BARRIER

CROSS-REFERENCE TO RELATED APPLICATIONS

This application is a National Phase of PCT/EP2020/062081, filed on Apr. 30, 2020, which claims priority to French Patent Application No. 1905566, filed on May 27, 2019, the disclosures of which are hereby incorporated by reference in their entireties.

TECHNICAL FIELD

The present invention relates to a pharmaceutical composition for its application as a drug, in particular for its use for the protection of the blood-brain barrier.

The present invention also relates to a pharmaceutical composition for its application as a drug, in particular for its use for the repair and/or restoration of the blood-brain barrier.

The present invention relates to a pharmaceutical composition for its application as a drug, in particular for its use for the protection and/or repair and/or restoration of the blood-brain barrier.

The present invention finds an application in particular in the therapeutic, pharmaceutical and veterinary fields.

In the description below, references in parentheses ( ) refer to the list of references presented at the end of the text.

STATE OF THE ART

The blood-brain barrier (BBB), also called the hemato-encephalic or hematomeningeal barrier, is made up of a monolayer of endothelial cells in the micro-vessels of the brain. These endothelial cells have tight junctions between them thus limiting the para- and transcellular exchanges between the blood compartment and the parenchymal compartment. The endothelial cells are surrounded by a basement membrane, astrocytic feet and pericytes thus reinforcing the BBB (Sharif et al., 2018 [16]). The basal lamina underlying the cerebral endothelium actively participates in the dynamics of the BBB, consists of 3 layers. The first, synthesized by endothelial cells, is characterized by the presence of laminin 4 and 5. The second is characterized by the presence of laminin-1 and -2, and is synthesized by astrocytes. The third, characterized by the presence of collagen IV, is found between the first two and is formed by the two cell types. These three layers are also made up of different types of collagen, glycoproteins and proteoglycans, in particular heparan sulphates proteoglycans (HSPGs) (Cardoso et al., 2010 [4]).

The basal lamina also contains numerous proteins, metalloproteases (MMPs) and their inhibitors which are involved in the dynamic regulation of BBB under physiological as well as pathological conditions.

BBB protects neurons against factors present in the systemic circulation and maintains the internal environment of the central nervous system, necessary for good synaptic and neuronal functioning (Sharif et al., 2018 [16]).

The alteration of BBB has been reported in many brain diseases such as Alzheimer's disease, Parkinson's disease, Huntington's disease, multiple sclerosis, cerebrovascular accident (CVA), chronic traumatic encephalopathy, but also brain infections (Abdullahi et al., 2018 [1]; Sweeney et al., 2018 [19]; Erickson and Banks 2018 [5]). The BBB is also impaired in the presence of brain tumors as well as following brain irradiation as part of radiotherapy (Katherine Elizabeth Warren, 2018 [22]). The disruption of BBB allows the influx into the brain of neurotoxic agents derived from blood, cells and microbial pathogens and is associated with inflammatory and immune responses, which can initiate and exacerbate several pathways of neuronal death (Sharif et al. 2018 [16]).

In the state of the art, there are therapeutic protocols and/or strategies aimed at protecting the components of the BBB structure: tight junctions and cell receptors; or at fighting against the causes of its permeability: inflammation; oxidation; activation of MMPs (Sifat et al., 2017 [17]). However, these therapeutic protocols and/or strategies have not demonstrated any real efficacy and/or a significant therapeutic effect, in particular for the protection of the BBB.

Other strategies for the protection of BBB have also been considered. For example, there are in the state of the art patent documents describing methods targeting molecules of cellular signaling pathways (delta-PKC) (patent application US20090062208A1); transcription factors (HMGB1) (application WO2018207792A1), the S100B protein (patent document CN101632728B), or even cell junctions (Claudin-5) (patent document CN105148276B) in association with the BBB. However, none of these methods and/or strategies has resulted in treatment or clinical application to date. In addition, in the state of the art, there are no products known to act directly as a protector or to promote the restoration of the BBB. In other words, there is currently no compound and/or pharmaceutical composition capable of protecting and/or repairing and/or restoring the blood-brain barrier.

Therefore, there is a real need in the state of the art to find a compound and/or a composition making it possible to protect the BBB, for example from lesions and/or alterations due, for example, to pathologies and/or treatment, for example, chemotherapy and/or radiotherapy, for example of the brain.

There is also a real need in the state of the art to find a compound and/or a composition making it possible to repair the alterations and/or lesions of the BBB, for example due to pathologies, for example Alzheimer's, Parkinson's, Huntington's diseases, multiple sclerosis, following a cerebrovascular accident (CVA), traumatic encephalopathy, for example chronic, cerebral infections, for example meningitis, for example viral or bacterial, alterations and/or lesions due, for example, to the presence of brain tumors, and/or treatment, for example chemotherapy and/or radiotherapy, for example of the brain.

There is also a real need in the state of the art to find a compound and/or a composition allowing a functional restoration of the BBB, for example after a lesion and/or deterioration of said BBB.

DESCRIPTION OF THE INVENTION

The object of the present invention is precisely to meet these needs by providing a pharmaceutical composition for its application or use as a drug for the protection and/or repair and/or restoration, preferably functional, of the blood-brain barrier, said composition comprising a biocompatible polymer of the following general formula (I)

$$AaXxYy \qquad (I)$$

in which:

A represents a monomer,

X represents an $R_1COOR_2$ group, or $—R_9(C{=}O)R_{10}$

Y represents an O or N-sulfonate group responding to one of the following formulas $—R_3QSO_3R_4$, $—R_5NSO_3R_6$, $—R_7SO_3R_8$ in which:

$R_1$, $R_3$, $R_5$ and Ry independently represent an aliphatic hydrocarbon chain, optionally branched and/or unsaturated and which, optionally, contains one or more aromatic rings with the exception of benzylamine and benzylamine sulfonate, $R_2$, $R_4$, $R_6$ and $R_8$ independently represent a hydrogen atom or an $M^+$ cation, and $R_7$ and $R_{10}$ independently represent a bond, an aliphatic hydrocarbon chain, optionally branched and/or unsaturated, a represents the number of monomers, x represents the degree of substitution of monomers A by X groups, y represents the degree of substitution of monomers A by Y groups.

The object of the present invention is precisely to meet these needs by providing a pharmaceutical composition for its use as a drug for the protection and/or repair and/or restoration, preferably functional, of the blood-brain barrier, said composition comprising a biocompatible polymer of the following general formula (I)

$$AaXxYy \quad (I)$$

in which:

A represents a monomer,

X represents an $R_1COOR_2$ group, or $—R_9(C{=}O)R_{10}$

Y represents an O or N-sulfonate group responding to one of the following formulas $—R_3QSO_3R_4$, $—R_5NSO_3R_6$, $—R_7SO_3R_8$ in which:

$R_1$, $R_3$, $R_5$ and $R_9$ independently represent an aliphatic hydrocarbon chain, optionally branched and/or unsaturated and which, optionally, contains one or more aromatic rings with the exception of benzylamine and benzylamine sulfonate, $R_2$, $R_4$, $R_6$ and $R_8$ independently represent a hydrogen atom or an $M^+$ cation, and $R_7$ and $R_{10}$ independently represent a bond, an aliphatic hydrocarbon chain, optionally branched and/or unsaturated, a represents the number of monomers, x represents the degree of substitution of monomers A by X groups, y represents the degree of substitution of monomers A by Y groups.

Advantageously, the inventor has unexpectedly demonstrated that the use of a biocompatible polymer according to the invention advantageously makes it possible to consolidate, strengthen and/or repair the blood-brain barrier (BBB).

In particular, the inventors have unexpectedly demonstrated that the use of a biocompatible polymer according to the invention advantageously allows, when the blood-brain barrier (BBB) has been altered, for example presents an inflammation and/or lesion and/or any alteration known to a person skilled in the art, whatever the cause or origin, to repair and/or strengthen and/or restore the blood-brain barrier (BBB).

The inventors have also demonstrated, surprisingly and unexpectedly, that the use of the polymer according to the invention advantageously makes it possible to accelerate and improve the functional recovery of the blood-brain barrier (BBB). In addition, the inventors have demonstrated, unexpectedly and surprisingly, that when the alteration of the BBB has an effect on motor and/or cognitive functions, the use of the polymer according to the invention also makes it possible to accelerate and/or improve functional motor and cognitive recovery.

As used herein, protection of the blood-brain barrier is understood to mean, for example, an improvement in the structure of the basement membrane of the blood-brain barrier and/or a stimulation of the endothelial cells of the blood-brain barrier and/or a strengthening of the tight junctions of the blood-brain barrier. Advantageously, the protection of the blood-brain barrier allows, for example, protection of the latter from external attacks, for example from ionizing radiation, for example from X-rays, gamma rays, from isotopic compounds, for example from xenobiotic compounds, various toxins. and pathogens. The protection of the blood-brain barrier can also make it possible to maintain the homeostasis of the central nervous system, for example regulation of ionic flow, and/or regulation of molecular and cellular flow, in particular between the blood compartment and the central nervous system. These flows can be deleterious for the central nervous system in the event of damage and permeability of said barrier.

As used herein, repair of the blood-brain barrier is understood to mean, for example, the reformation and/or improvement of the structure of the blood-brain barrier, for example when the structure of said barrier has been altered, for example due to a lesion, an external aggression, for example a pathogen, a disease, due to inflammation and/or any event known to a person skilled in the art, capable of altering and/or modifying the structure and/or function of the blood-brain barrier. This may be, for example, an acceleration of the healing of a lesion of the blood-brain barrier, a decrease in inflammation of the blood-brain barrier, healing and/or improvement of the basement membrane of the blood-brain barrier and/or endothelial cells of the blood-brain barrier and/or tight junctions of the blood-brain barrier.

As used herein, restoration of the blood-brain barrier is understood to mean structural repair and/or of reformation the blood-brain barrier and restoration/improvement of the blood-brain barrier function, for example of the permeability of the blood-brain barrier and/or of any physiological function of the blood-brain barrier.

In the present document, monomer is understood to mean, for example, a monomer selected among the group comprising sugars, esters, alcohols, amino acids or nucleotides.

In the present invention, the monomers A constituting the building blocks of the polymers of formula I may be the same or different.

In the present invention, the monomers A may independently be monomers of the following formula:

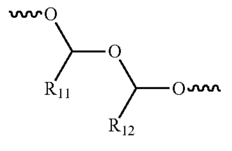

in which $R_{11}$ and $R_{12}$ independently represent an oxygen atom, an optionally branched and/or unsaturated aliphatic hydrocarbon chain, a heteroaryl group independently comprising one or more oxygen and/or nitrogen atoms, an aldehyde function, a carboxylic acid group, a diol, a substituted diol, a group of formula $—R_{13}—(X)n\text{-}R_{14}$ in which $R_{13}$ represents a $C_1$-$C_4$ aliphatic carbon chain, optionally branched and/or unsaturated, X represents a heteroatom selected among oxygen and nitrogen, is an integer ranging from 1 to 4 and $R_{14}$ is a hydrogen atom, an aliphatic hydrocarbon chain, optionally branched and/or unsaturated, a heteroaryl group independently comprising one or more oxygen atoms and/or nitrogen, an aldehyde function, a carboxylic acid group, a diol, a substituted diol.

In the present invention, the combination of monomers may make it possible to form a polymeric backbone, for example a polymeric backbone of polyester, polyalcohol, polysaccharide nature, of the nucleic acid or protein type.

In the present invention, among the polyesters, they may be, for example, copolymers of biosynthesis or chemical synthesis, for example aliphatic polyesters or of natural origin, for example polyhydroxyalkanoates.

In the present invention, the polysaccharides and their derivatives may be of bacterial, animal, fungal and/or plant origin. They may, for example, be single chain polysaccharides, for example polyglucoses, for example dextran, cellulose, beta glucan, or other monomers comprising more complex units, for example xanthans, for example glucose, mannose and glucuronic acid or also glucuronans and glucoglucuronan.

In the present invention, the polysaccharides of plant origin may be single chain, for example cellulose (glucose), pectins (galacturonic acid), fucans, starch, or more complex such as alginates (guluronic and mannuronic acid).

In the present invention, the polysaccharides of fungal origin may be, for example, steroglucan.

In the present invention, the polysaccharides of animal origin may be, for example, chitins or chitosan (glucosamine).

In the present invention, the monomers A constituting the basic elements of the polymers of formula I can advantageously be identical.

In the present invention, the monomers A constituting the basic elements of the polymers of formula I may advantageously be glucose.

The number of monomers A defined in formula (I) by "a" may be such that the mass of said polymers of formula (I) is approximately between 2,000 and 6,000 daltons, for example, which corresponds to at least 10 glucose monomers. For example, the mass of said polymers of formula (I) may approximately be between 3,000 and 6,000 daltons, for example, which corresponds to 12 to 20 glucose monomers.

The number of monomers A defined in formula (I) by "a" may also be such that the mass of said polymers of formula (I) is less than approximately 2,500,000 daltons (which corresponds to 7,000 glucose monomers). Advantageously, the mass of said polymers of formula (I) may be from 3,000 to 250,000 daltons, for example from 3,000 to 6,000 daltons, or, for example, from 20,000 to 250,000 daltons, or, for example, from 75,000 to 150,000 daltons.

In the present invention, in the —$R_1COOR_2$ group representing X, $R_1$ may be a $C_1$-$C_6$ alkyl, for example a methyl, an ethyl, a butyl, a propyl, a pentyl, preferably a methyl group, and $R_2$ may be a bond, a $C_1$-$C_6$ alkyl, for example a methyl, an ethyl, a butyl, a propyl, a pentyl, a group $R_{21}$ $R_{22}$ in which $R_{21}$ is an anion and $R_{22}$ a cation selected among the group of alkali metals.

Preferably, the group X is the group of formula —$R_1COOR_2$ in which $R_1$ is a methyl group —$CH_2$— and $R_2$ is a group $R_{21}$ $R_{22}$ in which $R_{21}$ is an anion and $R_{22}$ is a cation selected among the group of alkali metals, preferably the group X is a group of formula —$CH_2$—$COO^-$ or carboxymethyl.

In the present invention, in the group —$R_9(C{=}O)R_{10}$ representing X, $R_9$ may be a $C_1$-$C_6$ alkyl, for example a methyl, an ethyl, a butyl, a propyl, a pentyl, preferably a group methyl, and $R_{10}$ may be a bond, a $C_1$-$C_6$ alkyl, for example a methyl, an ethyl, a butyl, a propyl, a pentyl, a hexyl.

The degree of substitution of all the monomers A by X groups, defined in general formula (I) by "x", may be between 10 and 150%, 40 and 80%, and preferably of the order of 50% or 60%.

In the present invention, in the group corresponding to one of the following formulas —$R_3OSO_3R_4$, —$R_5NSO_3R_6$, —$R_7SO_3R_8$ and representing the Y group, $R_3$ may be a bond, a $C_1$-$C_6$ alkyl, for example a methyl, an ethyl, a butyl, a propyl, a pentyl, preferably a methyl group, $R_5$ may be a bond, a $C_1$-$C_6$ alkyl, for example a methyl, an ethyl, a butyl, a propyl, a pentyl, preferably a methyl group, $R_7$ may be a bond, a $C_1$-$C_6$ alkyl, for example a methyl, an ethyl, a butyl, a propyl, a pentyl, preferably a methyl group, $R_4$, $R_6$ and $R_8$ may independently be a hydrogen atom or an $M^+$ cation, for example $M^+$ may be an alkali metal.

Preferably, the Y group is the group of formula —$R_7SO_3R_8$ in which R7 is a bond and R8 is an alkali metal selected among the group comprising lithium, sodium, potassium, rubidium and cesium. Preferably, the Y group is a —$SO_3^-$ group, —$SO_3^-Na^+$.

The degree of substitution of all of the monomers A by the Y groups defined in general formula (I) by "y" may be from 10 to 170%, from 30 to 150%, from 55 to 160%, from 55 at 85%, from 120 to 160%, and preferably of the order of 70, 140 or 150%.

In the present invention, the definition of the above mentioned degrees of substitution is that a degree of substitution "x" of 100% means that each monomer A of the polymer of the invention statistically contains an X group. Likewise, a degree of substitution "y" of 100% means that each monomer of the polymer of the invention statistically contains a Y group. Degrees of substitution greater than 100% reflect the fact that each monomer statistically contains more than one group of the type considered; conversely, degrees of substitution of less than 100% reflect the fact that each monomer statistically contains less than one group of the type considered.

The polymers may also comprise functional chemical groups, designated Z, different from X and Y.

In the present invention, the Z groups may be the same or different, and may independently be selected among the group consisting of amino acids, fatty acids, fatty alcohols, ceramides, or derivatives thereof, or nucleotide sequences of addressing, antibodies, antibody fragments.

The Z groups may also represent identical or different active agents. These may be, for example, therapeutic agents, diagnostic agents, an anti-inflammatory, an antimicrobial, an antibiotic, a growth factor, an enzyme, an antioxidant compound, polyphenols, tannins, anthocyanins, lycopenes, terpenoids and resveratrol. In the present invention, the Z group may advantageously be a saturated or unsaturated fatty acid. It may, for example, be a fatty acid selected among the group comprising acetic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, trans-vaccenic acid, linoleic acid, linolelaidic acid, α-linolenic acid, γ-linolenic acid, dihomo-γ-linolenic acid, arachidonic acid, eicosapentaenoic acid, clupanodonic acid or docosahexaenoic acid. Preferably, the fatty acid is acetic acid.

In the present invention, the Z group may advantageously be an amino acid of the L or D series selected among the group comprising alanine, asparagine, an aromatic chain, for example tyrosine, phenylalanine, tryptophan, thyroxine or histidine. Preferably, the amino acid is phenylalanine.

In the present invention, the Z group may be an antioxidant, for example vitamin A, C, E, B9, B6, glutathione, selenium, polyphenols, for example catechins, for example green tea, flavonoids, tannins, anthocyanins, for example red fruits, lycopenes, terpenoids and resveratrol.

In the present invention, the Z group may be antiaging compounds, for example retinoids, allantoins.

In the present invention, the Z group may be antibodies, antibody fragments, for example Fab fragments. They may be, for example, antibodies and/or fragments of addressing antibodies, for example antibodies and/or fragments of antibodies capable of targeting the blood-brain barrier.

Advantageously, the Z groups can give the polymers additional biological or physicochemical properties. For example, the Z groups can increase the solubility or the lipophilicity of said polymer, for example allowing better diffusion or tissue penetration.

Advantageously, the Z groups can give the polymers additional biological or physicochemical properties. Thus, the polymers of the invention, for example when the Z group is selected among an antioxidant compound, an anti-aging compound, the polymers of the invention can advantageously convey these compounds and thus provide an additional and/or complementary biological effect.

Polymers in which Z is present may correspond to the following formula II: Aa Xx Yy Zz (II) in which, A, X, Y, a, x, y are as defined above and z represents the degree of substitution by Z groups.

In the present invention, the degree of substitution by Z groups represented by "z" may be between 1 and 50%, 10 and 25%, preferably equal to 15, 20 or 25%.

The X, Y and Z groups may be independently attached to the monomer A and/or independently attached to each other. When at least one of the X, Y and Z groups is independently attached to an X, Y and Z group different from the first, one of said X, Y or Z groups is attached to monomer A.

Thus, the Z groups may be covalently attached directly to the monomers A or covalently attached to the X and/or Y groups.

In the present invention, the Z groups may also be conjugated to the polymers of formula AaXxYy by bonds other than covalent, for example by ionic bonds, for example through ionic interactions, hydrophilic bonds or hydrophobic bonds. The polymers of the invention may then constitute a Z vectorization system.

In the present invention, the polymer may, for example, be a polymer selected among the group comprising the compounds OTR4120, OTR41201, OTR41202, OTR41203, OTR41205, OTR41210 OTR41301, OTR41302, OTR41303, OTR41305, OTR41310, OTR3131.

In the present document, the polymer may, for example, be a polymer selected among the group comprising the compounds OTR41201, OTR41202, OTR41203, OTR41205, OTR41210, OTR4120, OTR4122, OTR4125, OTR41301, OTR41302, OTR41303, OTR41305, OTR41310, OTR3131, OTR4132, OTR4135, OTR415 with the characteristics mentioned in Table 1 below.

TABLE 1

Polymers of the families Aa Xx Yy (1) and Aa Xx Yy Zz (II) in which A is glucose (MW 180D), X is Carboxymethyl (MW 58 D) Y: $SO_3^-$ (MW 80D) and Z is acetate (MW 43D) or phenylalanine (MW 165D).

| | | polymer | | | | |
|---|---|---|---|---|---|---|
| Name of RGTA | Average molecular weight M +/− 15% | A: glucose Starting Dextran Polymer (PM in daltons) | X —$CH_2COO$ CM/ glucose % of substitution | Y —$SO_3^-$ $SO_4$/ glucose) % of substitution | Z —$OCCH_3$ $OCCH_3$/ glucose % of substitution | Z phenylalanine |
| CMDS OTR41201 | 3,000 | 1,500 | 60 +/− 20 | 150 +/− 20 | 0 | |
| CMDS OTR41202 | 6,000 | 3,000 | 60 +/− 20 | 150 +/− 20 | 0 | |
| CMDS OTR41203 | 10,000 | 5,000 | 60 +/− 20 | 150 +/− 20 | 0 | |
| CMDS OTR41205 | 20,000 | 10,000 | 60 +/− 20 | 150 +/− 20 | 0 | |
| CMDS OTR41210 | 40,000 | 20,000 | 60 +/− 20 | 150 +/− 20 | 0 | |
| CMDS OTR4120 | 80,000 | 40,000 | 60 +/− 20 | 150 +/− 20 | 0 | |
| CMDS 0TR4122 | 220,000 | 110,000 | 60 +/− 20 | 150 +/− 20 | 0 | |
| CMDS OTR4125 | 500,000 | 250,000 | 60 +/− 20 | 150 +/− 20 | 0 | |
| CMDSA OTR41301 | 3,000 | 1,500 | 60 +/− 20 | 140 +/− 20 | 20 +/− 5 | |
| CMDSA OTR41302 | 6,000 | 3,000 | 60 +/− 20 | 140 +/− 20 | 20 +/− 5 | |
| CMDSA OTR41303 | 10,000 | 5,000 | 60 +/− 20 | 140 +/− 20 | 20 +/− 5 | |
| CMDSA OTR41305 | 20,000 | 10,000 | 80 +/− 20 | 140 +/− 20 | 20 +/− 5 | |
| CMDSA OTR41310 | 40,000 | 20,000 | 60 +/− 20 | 140 +/− 20 | 20 +/− 5 | |
| CMDSA OTR4131 | 80,000 | 40,000 | 60 +/− 20 | 140 +/− 20 | 20 +/− 5 | |

TABLE 1-continued

Polymers of the families Aa Xx Yy (1) and Aa Xx Yy Zz (II) in which A is glucose (MW 180D), X is Carboxymethyl (MW 58 D) Y: $SO_3^-$ (MW 80D) and Z is acetate (MW 43D) or phenylalanine (MW 165D).

| | | polymer | | | | |
|---|---|---|---|---|---|---|
| Name of RGTA | Average molecular weight M +/− 15% | A: glucose Starting Dextran Polymer (PM in daltons) | X —$CH_2COO$ CM/ glucose % of substitution | Y —$SO_3^-$ $SO_4$/ glucose) % of substitution | Z —$OCCH_3$ $OCCH_3$/ glucose % of substitution | Z phenylalanine |
| CMDSA OTR4132 | 220,000 | 110,000 | 60 +/− 20 | 140 +/− 20 | 20 +/− 5 | |
| CMDSA OTR4135 | 500,000 | 250,000 | 60 +/− 20 | 140 +/− 20 | 20 +/− 5 | |
| CMDSP OTR415 | 5,000 | | 60 +/− 20 | 70 +/− 15 | — | 15 +/− 5 |

In the present invention, the composition may comprise a concentration of 0.1 to 100 μg/ml by weight of biocompatible polymer relative to the volume of the composition. For example, the composition may comprise a concentration of 1 to 10 μg/ml by weight of biocompatible polymer relative to the total volume of the composition.

In the present invention, the composition may be formulated and/or adapted according to its administration. For example, for parenteral administration, the composition may be administered in order to deliver a dose of biocompatible polymer of 0.01 to 5 mg per kilogram of body weight, preferably 0.1 to 1.5 mg per kilogram of body weight at a frequency of one administration per week.

For example, for oral administration, the composition may be administered in order to deliver a dose of biocompatible polymer of 0.1 to 5 mg per kilogram of body weight, preferably 0.01 to 1.5 mg/kg at a frequency of daily or bi-weekly administration.

For sublingual administration, the intake may be daily or twice weekly and between 0.5 μg/kg and 100 μg/kg.

For example, for intraarterial administration, the biocompatible polymer may be at a concentration of from 0.1 to 100 μg/ml by weight of biocompatible polymer relative to the total volume of the composition, preferably from 1 to 20 ml.

Advantageously, when the composition and/or polymer is administered by the intraarterial route, the administration may be carried out in a route first in the brain, for example in the internal carotid artery.

For example, for intracranial injection, the biocompatible polymer may be at a concentration of from 0.1 to 100 μg/ml by weight of biocompatible polymer relative to the total volume of the composition, preferably from 5 to 20 μl.

Advantageously, when the composition and/or polymer is administered by the intracranial route, the administration may be carried out simultaneously or successively in different intracranial regions.

For example, for an intraventricular or intrathecal injection, the volume administered may be comprised from 5 μl to 2 ml, for example 500 μl, for example 2 ml. For example, for an intraventricular or intrathecal injection, the volume administered may be isovolumetric, for example up to 2 ml. For example, the volume administered may be as described in Marks et al., 2008 [10], Raffi et al, 2014 [13] and/or Blaney et al, 2004 [3].

For oral administration, for example in the form of a pill or capsule, the dose of biocompatible polymer may be between 0.0001 and 5 mg per kilogram of body weight.

For oral administration, for example in the form of a pill or capsule, the intake may be daily.

According to the invention, the molecular weight of the biocompatible polymer may range from 3,000 to 2,500,000 daltons.

For example, the molecular weight of the biocompatible polymer may be from 3,000 to 6,000 daltons, from 6,000 to 2,500,000 daltons, preferably from 20,000 to 250,000 daltons and, for example, from 75,000 to 150,000 daltons.

Advantageously, the molecular weight of the biocompatible polymers present in the composition may be selected according to the administration route of the composition and the frequency of administration. For example, for an injection by intravascular route, for example intraarterial, the molecular weight of the biocompatible polymer may be from 3,000 to 200,000 daltons depending on the level of damage of the blood-brain barrier lesion, preferably from 3,000 to 150,000 daltons.

Advantageously, the molecular weight of the biocompatible polymers present in the composition may be selected according to the deterioration and/or the state of the blood-brain barrier.

For example, when the blood-brain barrier undergoes significant structural alterations, for example to a lesion inducing a high permeability of the blood-brain barrier, the molecular weight of the biocompatible polymer can be from 3,000 to 200,000 daltons, preferably from 70,000 to 150,000 daltons.

Advantageously, the molecular weight of the biocompatible polymer may be adapted following and/or according to the progressive repair of the blood-brain barrier. For example, when the blood-brain barrier exhibits significant structural alterations, the molecular weight of the biocompatible polymer may be from 3,000 to 200,000 daltons, preferably from 70,000 to 150,000 daltons. Subsequently, the molecular weight used may be reduced, for example may be from 3,000 to 100,000 daltons, preferably from 10,000 to 70,000 daltons.

According to the invention, the composition may also comprise a hydrogel.

In the present document, hydrogel is understood to mean any suitable hydrogel known to a person skilled in the art. It may, for example, be a hydrogel selected among the group comprising hyaluronic acid or a derivative thereof, biocompatible hydrogels used in filling the brain space after injury. It may, for example, be a hydrogel described in the document Vladimir A. Kornev et al.: Hydrogel-assisted neuroregeneration approaches towards brain injury therapy: A state-of-the-art review. Computational and Structural Biotechnology Journal 16 j.csbj.2018.10.011 [24] and/or described in document Gopalakrishnan A, Shankarappa S A, Rajanikant G K. Hydrogel Scaffolds: Towards Restitution of Ischemic Stroke-Injured Brain 2019 February; 10(1):1-18 [25].

In the present document, the composition may comprise a hydrogel concentration of 0.1% to 5%, preferably 0.5% to 2.5% by weight of hydrogel.

According to the invention, the composition may comprise hyaluronic acid and/or at least one hydrogel and/or a mixture thereof.

In the present document, "hyaluronic acid" is understood to mean any hyaluronic acid known to a person skilled in the art, for example a non-sulfated linear glycosaminoglycan composed of repeating units of D-glucuronic acid and of N-acetyl-D-glucosamine. It may be, for example, hyaluronic acid (HA) in its acid form or in the form of salt (hyaluronate) of crosslinked hyaluronic acid. The HA is a non-sulphated linear glycosaminoglycan composed of repeating units of D-glucuronic acid and of N-acetyl-D-glucosamine (Tammi R., Agren U M., Tuhkanen A L., Tammi M. Hyaluronan metabolism in skin. Progress in Histochemistry & Cytochemistry. 29(2):1-81, 1994 [26]). It may be, for example, hyaluronic acid having average molecular weight fractions of 5,000 to 3,000,000 daltons, preferably between 50,000 and 2,000,000 daltons. In the present case, hyaluronic acid may be obtained by any method known to a person skilled in the art. These may, for example, be methods described in the journal Hyaluronan fragments: an information-rich system (R. Stern et al., European Journal of Cell Biology 58 (2006) 699-715 [27]). It may also be natural or modified hyaluronic acid, commercially available, whatever their designations and/or molecular weight, for example commercial hyaluronic acid selected among Hyactive CPN; Cristalhyal; Nutra HA; | Oligo HA; D Factor; Hyaluderm; juvelift; Restylane; Revitacare without this list being exhaustive. It may also be hyaluronic acid marketed by Contipro (https://www.contipro.com/portfolio/manufacturer-of-anti-ageing-cosmetic-raw-materials/HyActive") and/or Givaudan (https://www.givaudan.com/fragrances/active-beauty/products/cristalhyal%C2%AE-range).

In the present document, the composition may comprise a concentration of 0.1 to 5% by weight of hyaluronic acid relative to the total weight of the composition. For example, the composition may comprise a concentration of 0.5% to 2.5% by weight of hyaluronic acid relative to the total weight of the composition.

In the present document, the hydrogel composition may be formulated for administration by the direct intracranial route, for local intracranial injection, in particular by intraarterial route, the composition may comprise a concentration of 1 to 10 mg/ml by weight of hyaluronic acid relative to the total volume of the composition.

In the present document, the term "pharmaceutical composition" is understood to mean any form of pharmaceutical composition known to a person skilled in the art. In the present document, the pharmaceutical composition may be, for example, an injectable solution. It may be, for example, an injectable solution, for example for a local or systemic injection, for example in physiological serum, in injectable glucose solution, in the presence of excipients, for example dextrans, for example at concentrations known to a person skilled in the art, for example from one microgram to a few milligrams per ml. The pharmaceutical composition may be, for example, a drug intended for oral administration selected among the group comprising a liquid formulation, an effervescent oral dosage form, an oral powder, a multiparticulate system, an orodispersible dosage form.

For example, when the pharmaceutical composition is for oral administration, it may be in the form of a liquid formulation selected among the group comprising a solution, a syrup, a suspension or an emulsion. When the pharmaceutical composition is in the form of an effervescent oral dosage form, it may be in a form selected among the group comprising tablets, granules, powders. When the pharmaceutical composition is in the form of an oral powder or a multiparticulate system, it may be in a form selected among the group consisting of beads, granules, mini tablets and microgranules. When the pharmaceutical composition is in the form of an orodispersible dosage form, it may be in a form selected among the group consisting of orodispersible tablets, lyophilized wafers, thin films, a chewable tablet, a tablet, a capsule or a medical chewing gum.

According to the present invention, the pharmaceutical composition may be a pharmaceutical composition for oral administration, for example buccal and/or sublingual, for example selected among the group comprising buccal or sublingual tablets, lozenges, drops, a solution for sprays.

According to the present invention, the pharmaceutical composition may be a pharmaceutical composition for topical or transdermal administration, for example selected among the group comprising ointments, creams, gels, lotions, patches and foams.

According to the present invention, the pharmaceutical composition may be a pharmaceutical composition for nasal administration, for example selected among the group comprising nasal drops, nasal spray, nasal powder.

According to the present invention, the pharmaceutical composition may be a pharmaceutical composition for parenteral administration, for example subcutaneous, intramuscular, intravenous, intraarterial, intracranial, intrathecal. Preferably, the pharmaceutical composition may be a pharmaceutical composition for intraarterial and/or intracranial administration.

The composition of the present invention may also comprise at least one other active ingredient, particularly another therapeutically active ingredient, for example for simultaneous, separate or staggered use over time depending on the galenic formulation used. This other ingredient may be, for example, an active ingredient used, for example, in the treatment of opportune diseases which may develop in a patient having an alteration and/or damage to the blood-brain barrier. They may also be pharmaceutical products known to a person skilled in the art, for example antibiotics, anti-inflammatories anticoagulants, neuroprotectors, acetylcholinesterase inhibitors, antidepressants, antivirals.

According to the invention, the composition may be, for example, administered daily, twice daily and weekly. It may be, for example, an administration once a day, twice a day or more.

According to the invention, the composition may be, for example, administered over a period of 1 day to 3 months, for example for 2 months. For example, the composition may be administered over a period of 3 months with a daily frequency of administration.

An object of the present invention is also the use of a pharmaceutical composition comprising a biocompatible polymer of formula AaXxYy (I) or AaXxYyZz (II) for the manufacture of a drug for protection and/or repair/restoration of the blood-brain barrier.

The biocompatible polymer is as defined above.

In this embodiment, the term drug is understood to mean a pharmaceutical composition as defined above.

Advantageously, the inventors demonstrated that the biocompatible polymer makes it possible, unexpectedly, both to accelerate the repair/reformation of the blood-brain barrier when the latter is altered, both at the structural and/or functional level. In addition, the inventors demonstrated that the biocompatible polymer, advantageously and unexpectedly, allows a functional restoration of the blood-brain barrier, in particular a restoration of its permeability, whatever the cause and/or the origin of its modification and/or alteration.

Figure 1:
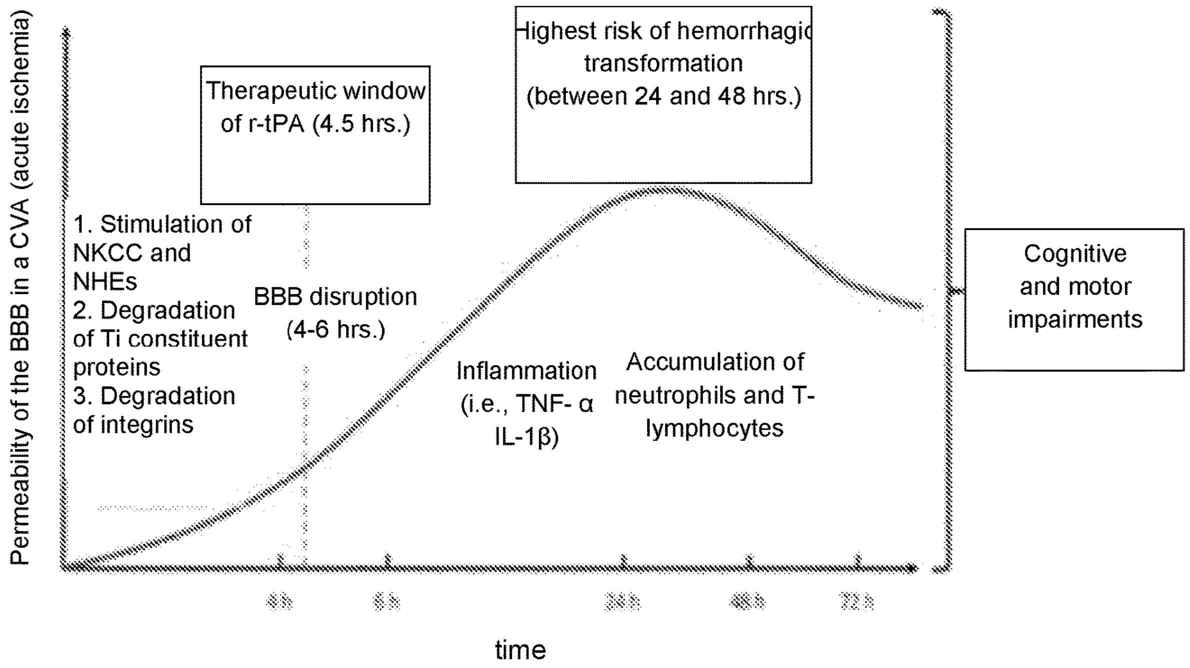
FIG. 1 represents the evolution of the permeability of the blood-brain barrier (BBB) after an ischemic vascular accident according to time; the ordinate corresponds to the permeability and the abscissa to the time in hours.

Other advantages may also appear to a person skilled in the art on reading the examples below, illustrated by the appended figures, given by way of illustration.

EXAMPLES

Example 1: Use of a Biocompatible Polymer for the Treatment of an Impaired Blood-Brain Barrier and Functional Restoration of the Blood-Brain Barrier A/Preparation of Biocompatible Polymers.

The synthesis of biocompatible polymers, RGTA, is widely described in the prior art, for example in U.S. Pat. No. 7,396,923 entitled "Process for the sulfonation of compounds comprising free hydroxyl (OH) groups or primary or secondary amines" and also in the bibliographic reference Yasunori I. et al., Biomaterials 2011, 32: 769e776) and Petit E. et al., Biomacromolecules. 2004 March-April; 5(2):445-52 [28].

Several RGTAs are known and have been described, including the OTR4120 describes numerous preclinical and clinical publications (RGTA®-based matrix therapy-A new branch of regenerative medicine in locomotion. Barritault D, Desgranges P, Meddahi-Pellé A, Denoix J M, Saffar J L. Joint Bone Spine. 2017 May; 84(3):283-292. DOI: 10.1016/j.jbspin.2016.06.012 [29], RGTA® or ReGeneraTing Agents mimic heparan sulfate in regenerative medicine: from concept to curing patients Barritault D, Gilbert-Sirieix M, Rice K L, Sineriz F, Papy-Garcia D, Baudouin C, Desgranges P, Zakine G, Saffar J L, van Neck J. Glycoconj J. 2017 June; 34 (3): 325-338. DOI: 10.1007/s10719-016-9744-5 [2]. The compound OTR4131 is a compound comprising a radical Z which is a fatty acid, namely acetic acid as described in Frescaline G. et al., Tissue Eng Part A 2013 July; 19 (13-14): 1641-53. DOI: 10.1089/ten.TEA.2012.0377 [30]), Randomized controlled trial demonstrates the benefit of RGTA® based matrix therapy to treat tendinopathies in racing horses. Jacquet-Guibon S, Dupays A G, Caudry V, Crevier-Denoix N, Leroy S, Sineriz F, Chiappini F, Barritault D, Denoix J M. PLoS One. 2018 Mar. 9; 13 (3): e0191796. DOI: 10.1371/journal.pone.0191796 [31]. Other compounds also described in patent documents U.S. Pat. No. 6,689,741, US2014301972A 1 in which Z is an amino acid such as phenylalanine (Heparan sulfate proteoglycans mediate internalization and propagation of specific proteopathic seeds. Holmes B B, DeVos S L, Kfoury N, Li M, Jacks R, Yanamandra K, Ouidja M O, Brodsky F M, Marasa J, Bagchi D P, Kotzbauer P T, Miller T M, Papy-Garcia D, Diamond M I. Proc Natl Acad Sci USA 2013 Aug. 13; 110 (33): E3138-47. DOI: 10.1073/pnas.1301440110 [32]) or other hydrophobic compound (Structure-activity studies of heparan mimetic polyanions for anti-prion therapies. Ouidja M O, Petit E, Kerros M E, Ikeda Y, Morin C, Carpentier G, Barritault D, Brugère-Picoux J, Deslys J P, Adjou K, Papy-Garcia D. Biochem Biophys Res Commun. 2007 Nov. 9; 363 (1): 95-100 [33]).

B/Functional Restoration of the Blood-Brain Barrier with a Biocompatible Polymer In the present example, an evaluation of the effects of the biocompatible polymer according to the invention, RGTA, on the permeability of the BBB after alteration, for example following a cerebrovascular accident (CVA).

In this example, a rat CVA model was used. It was a cerebral ischemia of 1 hour, obtained by occlusion of the cerebral artery by intraluminal route followed by reperfusion. The rats used were male Sprague Dawley rats with an average weight of 300-350 g. The number of rats used was four to six rats per group per time. In this model, it is well known that the permeability of the BBB gradually increases to reach a peak at 24-48 h after the induction of cerebral ischemia (Garrigue et al. 2016 [6]; Sharif et al., 2018 [16]). FIG. 1 represents the change in permeability according to time in the model used as described in Abdullahi et al., 2018.

The BBB permeability evaluation was carried out by MRI after an injection of a contrast agent, Dotarem®, at different times: 1 h, 3 h, 24 h, 48 h, and 7 days after the cerebral ischemia. This contrast agent does not cross the BBB under physiological conditions. The contrast agent was injected intravenously, through the femoral vein. The amount of contrast agent administered by injection was 200 μmol/kg (Dotarem (registered trademark), Guerbet S.A).

Figure 2:
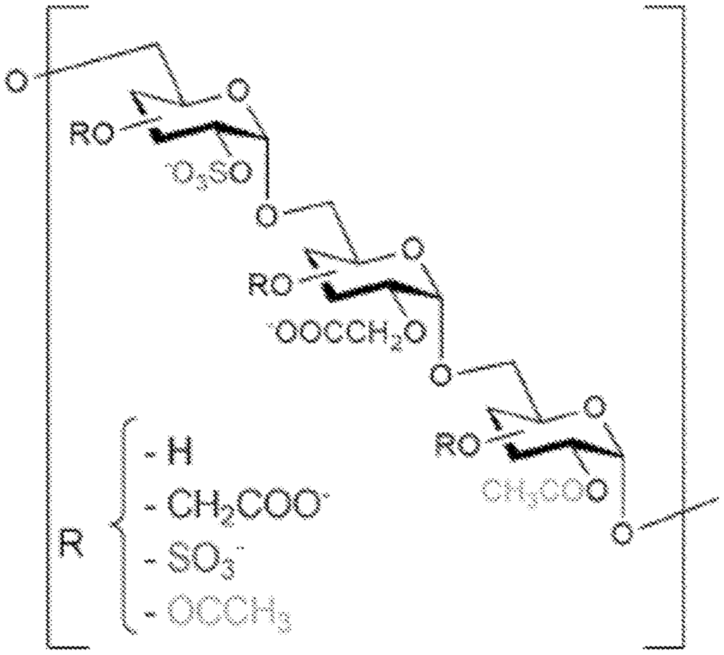
FIG. 2 represents an example of the structure of a biocompatible polymer, for example the structure of the compound OTR4132.

Rats, namely four to five animals per group and per time, were treated with a biocompatible polymer, namely RGTA OTR4132 with a molecular weight of 100,000 to 150,000 Da. FIG. 2 represents the structure of said polymer. The biocompatible polymer OTR4132 was administered 1 hour after cerebral ischemia, the volume of composition administered comprising a concentration of 0.5 mg/kg of OTR4132 was 300 μl per tail vein.

Rats, namely four to five animals per group and per time were treated with a control solution i.e., physiological serum (0.9% NaCl saline solution). The control solution was administered in an identical manner to the composition comprising the compound OTR4132, namely 1 hour after cerebral ischemia, the volume of composition administered being 250 μl administered by the femoral vein.

The observation of the permeability and the diffusion of the contrast agent was carried out by observation on images obtained by MRI. The region's of the central nervous system observed were located in the cerebral hemisphere affected by ischemia as well as in the healthy contralateral hemisphere. The determination of the diffusion of the contrast agent on the images obtained was carried out by MRI analysis using appropriate software (Image J (trademark) (Wayne Rasband, NIMH, Maryland, USA)). Diffusion of the contrast agent and/or permeability of the blood-brain barrier are shown in FIG. 3.

Figure 3:
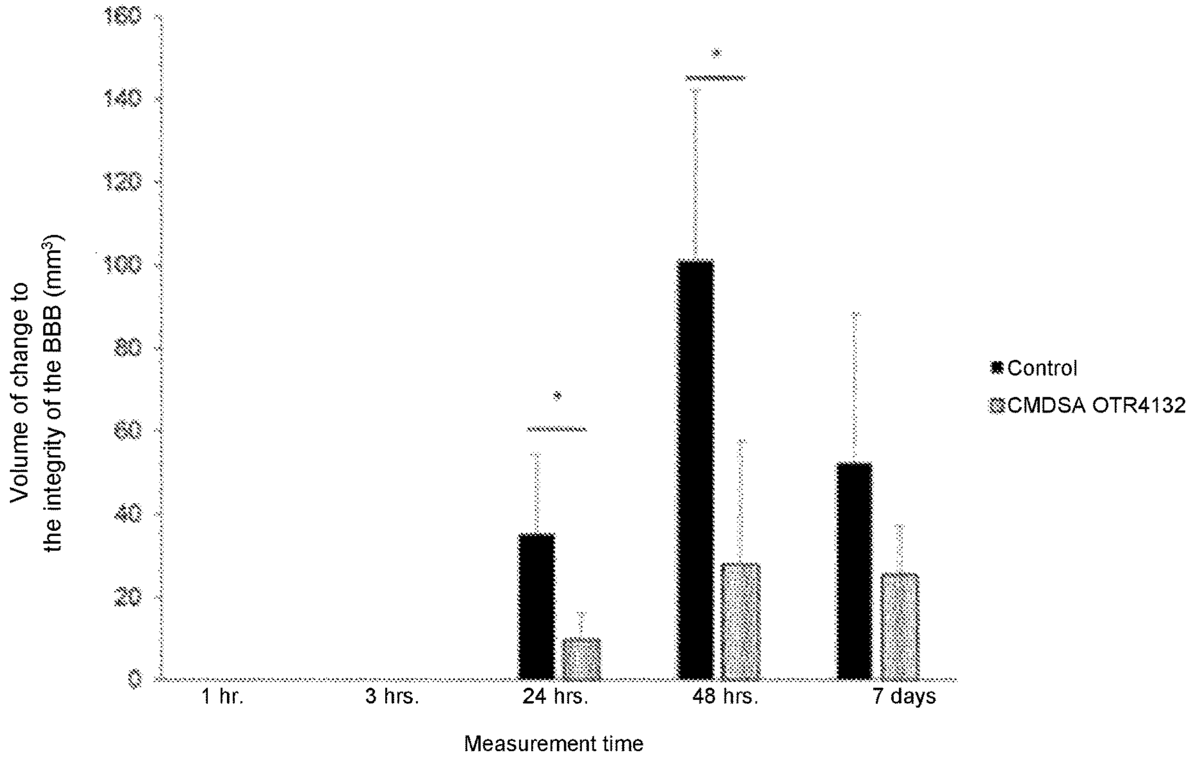
FIG. 3 is a bar graph showing the evolution of BBB permeability in regions of interest studied by MRI. In this figure, the abscissa corresponds to the time in hours or days after cerebral ischemia: 1 h, 3 h, 24 h, 48 h, and 7 days after ischemia. The values obtained correspond to the mean+/− standard deviation. In this figure, the ordinate corresponds to the volume of modification of the integrity of the BBB in $mm^3$. The values obtained for rats for which a composition comprising a biocompatible polymer (OTR4132) was administered are represented by white bars, the values obtained for rats for which a control composition was administered are represented by black bars.

As shown in the diagram of FIG. 3, the rats given the contrast agent and the control solution show an increased permeability of the blood-brain barrier 24 hours, 48 hours and 7 days after the CVA (black bars); these results were in agreement with those obtained in the state of the art (Garrigue et al. 2016 [6]). This diagram also clearly and unexpectedly demonstrates that the treatment of the rats with the biocompatible polymer OTR4132 makes it possible to significantly reduce the permeability of the BBB at 24 and 48 h post-ischemia in the group of rats treated with RGTA compared to the rats of the ischemic group that received the control solution. In particular, the results demonstrated a statistically significant difference between the rats treated with a control solution compared to the rats treated with a composition comprising a biocompatible polymer according to the invention (ANOVA followed by a post-hoc HSD test by Tukey $p<0.05$).

The results obtained and illustrated in FIG. 3 clearly demonstrate that the use of biocompatible polymers according to the invention makes it possible to preserve the integrity of the BBB after a CVA. In particular, these results clearly demonstrate that the use of a biocompatible polymer according to the invention makes it possible both to protect the BBB, to promote its repair and, in the case where the physiological properties of the BBB are altered/modified, to restore physiological properties and/or reduce their changes.

In addition to the results obtained by MRI, the permeability of the BBB was measured by staining with Evans blue after induction of cerebral ischemia according to the method described in the document Hone et al., 2018 [7]. The rats used were male Sprague Dawley rats with an average weight of 300-350 g, the experiment was carried out on 11 rats including five rats for which Evans blue, which does not cross the BBB under physiological conditions, was injected intravenously at a concentration of 2%, 72 h after cerebral ischemia, the volume injected being 4 ml/kg, i.e., 1.2 to 1.4 ml for a rat weighing 300 to 350 g respectively.

Six rats had been treated with a biocompatible polymer, namely RGTA OTR4132 with a molecular weight of 100,000 to 150,000 Da, administered 1 hour after cerebral ischemia, the volume of composition administered comprising a dose of 2.22 μg of OTR4132 were 50 μl intraarterially through the internal carotid.

Five rats had been treated with a control solution, namely physiological serum (0.9% NaCl saline solution) administered in an identical manner to the composition comprising the compound OTR4132, namely 1 hour after the cerebral ischemia, the volume of composition administered being 50 μl intraarterially through the internal carotid.

Thirty minutes after the administration of Evans blue, an intracardiac infusion with physiological saline was performed on the animal, the brain was removed and the hemispheres separated. The samples were then ground in phosphate buffered saline and then placed at 4° C. in the presence of 60% trichloroacetic acid. The samples were then centrifuged (1,000 g for 30 minutes) and the supernatant collected for a spectrophotometer reading at 610 nm. In parallel, an ascending concentration range of Evans blue was prepared.

The tissue Evans blue present in the collected supernatant was then quantified by spectrophotometry with a measurement at 610 nm.

Figure 4:
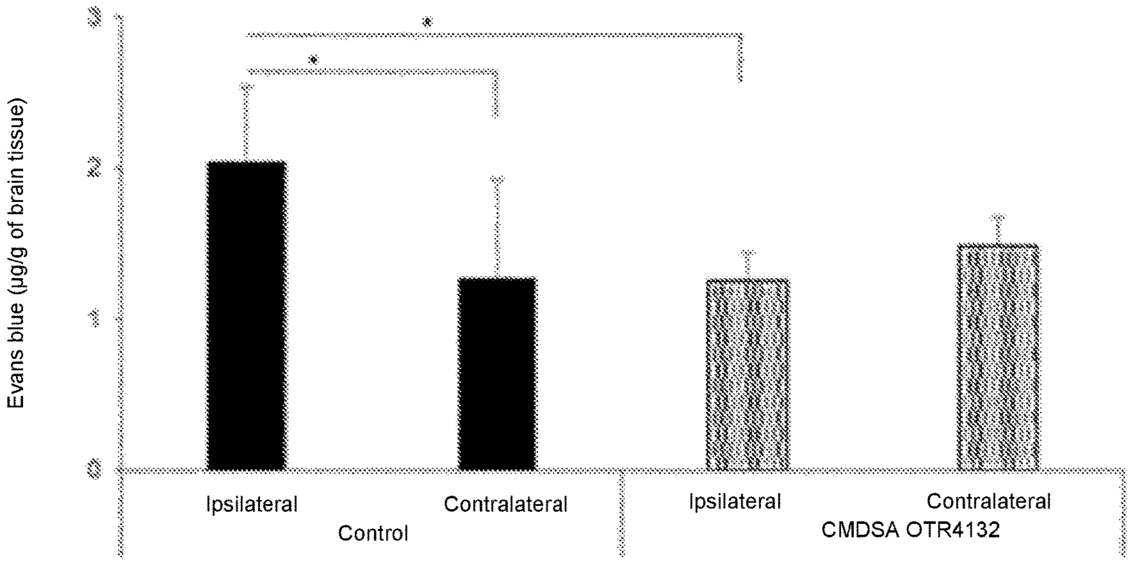
FIG. 4 is a bar graph showing the permeability of the BBB after cerebral ischemia by Evans blue staining. In this figure, the ordinate represents the quantity of Evans blue in μg/g of cerebral tissue according to the ischemic region of the central nervous system, namely ipsilateral or contralateral. The values obtained for rats for which a composition comprising a biocompatible polymer (OTR4132) was administered are represented by gray bars, the values obtained for rats for which a control composition was administered are represented by black bars.

FIG. 4 represents the results obtained according to the individuals. The results obtained in the group of control animals show a significant alteration in the permeability of the BBB in the ipsilateral hemisphere compared to the contralateral hemisphere (2-way ANOVA (p group=0.1582; p hemisphere=0.0933; p group*hemisphere=0.0175) followed by a Tukey HSD post hoc test p=0.0374). Unexpectedly, no difference was observed between the ipsilateral and contralateral hemispheres in the group of animals treated with the biocompatible polymer OTR4132 (2-way ANOVA (p group=0.1582; p hemisphere=0.0933; p group *hemisphere=0.0175) followed by a Tukey HSD post hoc test p=0.9965). In addition, the analyzes also demonstrate a statistically significant decrease in the alteration of the BBB in the ipsilateral hemisphere of the animals treated with the biocompatible polymer OTR4132 compared to the control animals (2-way ANOVA (p group=0.1582; p hemisphere=0.0933; p group*hemisphere=0.0175) followed by a Tukey HSD post hoc test p=0.0439).

This example clearly demonstrates that examples of a composition according to the invention comprising a polymer of formula AaXxYy or AaXxYyZz advantageously makes it possible to protect the BBB and/or to restore the physiological properties of the BBB. In particular, this example clearly demonstrates that examples of a composition according to the invention comprising a polymer of formula AaXxYy or AaXxYyZz make it possible to preserve the integrity of the BBB after a CVA. In particular, these results clearly demonstrate that the use of a biocompatible polymer according to the invention makes it possible both to protect the BBB, to promote its repair, and, in the case where the physiological properties of the BBB are altered/modified, to restore physiological properties and/or reduce their changes.

Example 2: Use of a Biocompatible Polymer for the Treatment of an Altered Blood-Brain Barrier and Functional Restoration of the Blood-Brain Barrier An individual, a 75-year-old man (75 kg) suffering from neurological disorders, in particular cognitive disorders, attributed to several CVAs as noted by neurologists, which altered the blood-brain barrier, was treated with a biocompatible polymer, namely the compound OTR4120, a daily intake of 30 ml of a 100 μg/ml aqueous solution of OTR4120 over 45 days. The dose administered was 3 mg/day/for 75 kg or 40 μg/kg/day. Following the administration, an improvement in cognitive performance was observed by neurologists and also by the attending or referring physician and the individual's family.

Another individual, an 85-year-old woman with major memory problems, in particular difficulty in reading and recognizing individuals, particularly close relatives (families), inability to write, etc. The individual (weighing about 60 kg), diagnosed as having Alzheimer's with handicap coefficient thus implicating an alteration of the blood-brain barrier, was treated by twice-weekly sublingual intake of a dose of OTR4120 from 300 microL to 100 μg/ml or 0.5 μg (0.5 μg/kg twice weekly). After treatment for 6 months, the individual showed an improvement in cognitive functions, social relations, for example with her environment, especially relatives and medical personnel, was able to telephone, go out, see friends, play scrabble, etc. These improvements were in particular linked to an improvement and recovery of the functions of the blood-brain barrier.

REFERENCES

1. Abdullahi W, Tripathi D, Ronaldson PT. Blood-Brain Barrier Dysfunction in Ischemic Stroke: Targeting Tight Junctions and Transporters for Vascular Protection. Am J Physiol Cell Physiol. 2018 Jun. 27. doi: 10.1152/ajpce11.00095.2018. [Epub ahead of print] PubMed PMID: 29949404
2. Barritault D, Gilbert-Sirieix M, Rice K L, Siñeriz F, Papy-Garcia D, Baudouin C, Desgranges P, Zakine G, Saffar J L, van Neck J. RGTA® or ReGeneraTing Agents mimic heparan sulfate in regenerative medicine: from concept to curing patients. Glycoconj J. 2017 June; 34(3): 325-338. doi: 10.1007/s10719-016-9744-5. Epub 2016 Dec. 7. Review. PubMed PMID: 27924424; PubMed Central PMCID: PMC5487810.
3. Blaney, S. M., Balis, F. M., Berg, S., Arndt, C. A., Heideman, R., Geyer, J. R., & Aikin, A. (2005). Intrathecal mafosfamide: a preclinical pharmacology and phase I trial. *Journal of clinical oncology,* 23(7), 15551563.
4. Cardoso, F. L., Brites, D., & Brito, M. A. (2010). Looking at the blood-brain barrier: molecular anatomy and possible investigation approaches. *Brain research reviews,* 64(2), 328-363.
5. Erickson M A. and Banks W A. Neuroimmune Axes of the Blood-Brain Barriers and Blood-Brain Interfaces: Bases for Physiological Regulation, Disease States, and Pharmacological Interventions. Pharmacol Rev. 2018 April; 70(2):278-314. doi: 10.1124/pr.117.014647. Review.
6. Garrigue P, Giacomino L, Bucci C, Muzio V, Filannino M A, Sabatier F, Dignat-George F, Pisano P, Guillet B. Single photon emission computed tomography imaging of cerebral blood flow, blood-brain barrier disruption, and apoptosis time course after focal cerebral ischemia in rats. Int J Stroke. 2016 January; 11(1):117-26.
7. Hone E A, Hu H, Sprowls S A, Farooqi I, Grasmick K, Lockman P R, et al. Biphasic Blood-Brain Barrier Openings after Stroke. Neurol Disord Stroke Int. 2018; 1(2): 1011.
8. Hynes R O, Naba A. Overview of the matrisome—an inventory of extracellular matrix constituents and functions. Cold Spring Harb Perspect Biol. 2012 Jan. 1; 4(1):a004903. doi: 10.1101/cshperspect.a004903. Review. PubMed PMID: 21937732; PubMed Central PMCID: PMC3249625.
9. Khelif, Y., Toutain, J., Quittet, M. S., Chantepie, S., Laffray, X., Valable, S., & Barritault, D. (2018). A heparan sulfate-based matrix therapy reduces brain damage and enhances functional recovery following stroke. Theranostics, 8(21), 5814.
10 Marks Jr, W. J., Ostrem, J. L., Verhagen, L., Starr, P. A., Larson, P. S., Bakay, R. A., . . . & Bartus, R. T. (2008). Safety and tolerability of intraputaminal delivery of CERE-120 (adeno-associated virus serotype 2-neurturin) to patients with idiopathic Parkinson's disease: an open-label, phase I trial. *The Lancet Neurology,* 7(5), 400-408.
11. Möbius-Winkler, S., Linke, A., Adams, V., Schuler, G., & Erbs, S. (2010). How to improve endothelial repair mechanisms: the lifestyle approach. Expert review of cardiovascular therapy, 8(4), 573-580.
12. Peschillo S, Diana F, Berge J, Missori P. A comparison of acute vascular damage caused by ADAPT versus a stent retriever device after thrombectomy in acute ischemic stroke: a histological and ultrastructural study in an animal model. J Neurointery Surg. 2017 August; 9(8): 743-749. doi: 10.1136/neurintsurg-2016-012533. Epub 2016 Jul. 7. PubMed PMID: 27387708. PMID: 11152991.
13. Rafii, M. S., Baumann, T. L., Bakay, R. A., Ostrove, J. M., Siffert, J., Fleisher, A. S., & Chu, Y. (2014). A phase1 study of stereotactic gene delivery of AAV2-NGF for Alzheimer's disease. Alzheimer's & Dementia, 10(5), 571-581.
14. Rajendran P, Rengarajan T, Thangavel J, Nishigaki Y, Sakthisekaran D, Sethi G, Nishigaki I. The vascular endothelium and human diseases. Int J Biol Sci. 2013 Nov. 9; 9(10):1057-69. doi: 10.7150/ijbs.7502. eCollection 2013. Review. PubMed PMID: 24250251; PubMed Central PMCID: PMC3831119.
15. Ronaldson, P. T., & Davis, T. P. (2015). Targeting transporters: promoting blood-brain barrier repair in response to oxidative stress injury. Brain research, 1623, 39-52.
16. Sharif Y, Jumah F, Coplan L, Krosser A, Sharif K, Tubbs R S. The Blood Brain Barrier: A Review of its Anatomy and Physiology in Health and Disease. Clin Anat. 2018 Apr. 10. doi: 10.1002/ca.23083. [Epub ahead of print] PubMed PMID: 29637627.
17. Sifat, A. E., Vaidya, B., & Abbruscato, T. J. (2017). Blood-brain barrier protection as a therapeutic strategy for acute ischemic stroke. The AAPS journal, 19(4), 957-972.
18. Steiner E, Enzmann G U, Lyck R, Lin S, Ruegg M A, Kroger S, and Engelhardt B. The heparan sulfate proteoglycan agrin contributes to barrier properties of mouse brain endothelial cells by stabilizing adherens junctions. Cell Tissue Res 358:465-479, 2014.
19. Sweeney M D, Sagare A P, Zlokovic B V. Blood-brain barrier breakdown in Alzheimer disease and other neurodegenerative disorders. Nat Rev Neurol. 2018 March; 14(3):133-150. doi: 10.1038/nrneuro1.2017.188. Epub 2018 Jan. 29. Review. PubMed PMID: 29377008; PubMed Central PMCID: PMC5829048.
20. Teng D, Pannell J S, Rennert R C, Li J, Li Y S, Wong V W, Chien S, Khalessi A A. Endothelial trauma from mechanical thrombectomy in acute stroke: in vitro live-cell platform with animal validation. Stroke. 2015 April; 46 (4): 1099-106. doi: 10.1161/STROKEAHA.114.007494. Epub 2015 Feb. 24. PubMed PMID: 25712942.
21. Thomsen M S, Routhe L J, Moos T. The vascular basement membrane in the healthy and pathological brain. J Cereb Blood Flow Metab. 2017 October; 37(10): 3300-3317. doi: 10.1177/0271678X17722436. Epub 2017 Jul. 28. Review.
22. Warren, K, E Beyond the Blood: Brain Barrier: The Importance of Central Nervous System (CNS) Pharmacokinetics for the Treatment of CNS Tumors, Including Diffuse Intrinsic Pontine Glioma Front. Oncol., 3 Jul. 2018|https://doi.org/10.3389/fonc.20. Review
23. Wilgus A. 2012 Growth Factor-Extracellular Matrix Interactions Regulate Wound Repair. Advances in Wound Care, 1 (6): 249-254. doi: 10.1089/wound.2011.0344.
24. Vladimir A. Kornev et al: Hydrogel-assisted neuroregeneration approaches towards brain injury therapy: A state-of-the-art review. Computational and Structural Biotechnology Journal 16 j.csbj.2018.10.011.
25. Gopalakrishnan A, Shankarappa S A, Rajanikant G K. Hydrogel Scaffolds: Towards Restitution of Ischemic Stroke-Injured Brain 2019 February; 10(1):1-18.
26. Tammi R., Agren UM., Tuhkanen AL., Tammi M. Hyaluronan metabolism in skin. Progress in Histochemistry & Cytochemistry. 29(2):1-81, 1994
27. R. Stern et al., European Journal of Cell Biology 58 (2006) 699-715.
28. Yasunori I. et al., Biomaterials 2011, 32: 769e776) et Petit E. et al., Biomacromolecules. 2004 March-April; 5(2):445-52
29. RGTA®-based matrix therapy-A new branch of regenerative medicine in locomotion. Barritault D, Desgranges P, Meddahi-Pellé A, Denoix J M, Saffar J L. Joint Bone Spine. 2017 May; 84(3):283-292. doi: 10.1016/j.jbspin.2016.06.012
30. Frescaline G. et al., Tissue Eng Part A. 2013 July; 19(13-14):1641-53. doi: 10.1089/ten.TEA.2012.0377
31. Randomized controlled trial demonstrates the benefit of RGTA® based matrix therapy to treat tendinopathies in racing horses. Jacquet-Guibon S, Dupays A G, Coudry V, Crevier-Denoix N, Leroy S, Siñeriz F, Chiappini F, Barritault D, Denoix J M. PLoS One. 2018 Mar. 9; 13(3): e0191796. doi: 10.1371/journal.pone.0191796
32. Heparan sulfate proteoglycans mediate internalization and propagation of specific proteopathic seeds. Holmes B B, DeVos S L, Kfoury N, Li M, Jacks R, Yanamandra K, Ouidja M O, Brodsky F M, Marasa J, Bagchi D P, Kotzbauer P T, Miller T M, Papy-Garcia D, Diamond M I. Proc Natl Acad Sci USA. 2013 Aug. 13; 110(33): E3138-47. doi: 10.1073/pnas.1301440110
33. Structure-activity studies of heparan mimetic polyanions for anti-prion therapies. Ouidja M O, Petit E, Kerros M E, Ikeda Y, Morin C, Carpentier G, Barritault D, Brugère-Picoux J, Deslys J P, Adjou K, Papy-Garcia D. Biocshem Biophys Res Commun. 2007 Nov. 9; 363(1):95-100

The invention claimed is:

1. A method for the protection of the blood-brain barrier from external attacks selected from an isotopic compound, a toxin and/or a pathogen, comprising administering a pharmaceutical composition comprising: a biocompatible polymer of the following general formula (I)

$$AaXxYyZz \qquad (I)$$

in which:

A is glucose,

X represents an $R_1COOR_2$ group, in which R1 is a methyl group —$CH_2$— and R2 is a group R21 R22 in which R21 is an anion and R22 is a cation which is an alkali metal or X is —CH2COO—, Y represents —$R_7SO_3R_8$ in which R7 is a bond and R8 is an alkali metal selected from the group consisting of lithium, sodium, potassium, rubidium and cesium or Y is a —SO3- group, Z is phenylalanine or acetate;

a represents the number of monomers, x represents the degree of substitution of monomers A by X groups, y represents the degree of substitution of monomers A by Y groups, wherein x is between 10 and 150%, wherein the degree of substitution "y" is between 10 and 170%, and wherein the degree of substitution of all the monomers A by Z groups represented by "z" is between 1 and 50%, to an individual at risk from external attacks selected from an isotopic compound, a toxin and/or a pathogen; wherein the pharmaceutical composition is administered orally, nasally, subcutaneously, intramuscularly, intravenously, intraarterially, intracranially, or intrathecally.

2. The method of claim 1, wherein the pharmaceutical composition further comprises hyaluronic acid.

3. The method of claim 1, wherein the number of monomer "a" is such that the mass of said polymers of formula (I) is greater than or equal to 2,000 daltons.

4. The method of claim 1, wherein said pharmaceutical composition is administered orally at a dose of 0.1 to 5 mg/kg of body weight, and/or intracranially at a dose of 0.1 to 100 $\mu g \cdot ml^{-1}$.

5. The method of claim 2, wherein the concentration of hyaluronic acid is from 1 to 10 mg/ml.

6. The method of claim 1, wherein Z is phenylalanine.

7. The method of claim 1, wherein Z is acetate.

8. The method of claim 1, wherein X is —CH2-COO—, Y is a —SO3- group, and Z is phenylalanine.

9. The method of claim 1, wherein X is —CH2-COO—, Y is a —SO3- group, and Z is acetate.

10. A method for the protection and/or repair/restoration of the blood-brain barrier, comprising identifying or selecting an individual who has an altered blood-brain barrier, and administering a pharmaceutical composition comprising: a biocompatible polymer of the following general formula (I)

$$AaXxYyZz \qquad (I)$$

in which:

A is glucose,

X represents an $R_1COOR_2$ group, in which R1 is a methyl group —$CH_2$— and R2 is a group R21 R22 in which R21 is an anion and R22 is a cation is an alkali metal or X is —CH2-COO—, Y represents —$R_7SO_3R_8$ in which R7 is a bond and R8 is an alkali metal selected from the group consisting of lithium, sodium, potassium, rubidium and cesium or Y is a —SO3- group, Z is phenylalanine, a represents the number of monomers, x represents the degree of substitution of monomers A by X groups, y represents the degree of substitution of monomers A by Y groups, wherein x is between 10 and 150%, wherein the degree of substitution "y" is between 10 and 170%, and wherein the degree of substitution of all the monomers A by Z groups represented by "z" is between 1 and 50%, to the individual.

11. The method of claim 10, wherein X is —CH2-COO—, Y is a —SO3- group.

* * * * *